United States Patent [19]

DiGiovanna et al.

[11] Patent Number: 5,036,530
[45] Date of Patent: Jul. 30, 1991

[54] EMISSION TOMOGRAPHY CAROUSEL SYSTEM AND METHOD

[75] Inventors: Leonard D. DiGiovanna, West Hempstead; Patrick F. Panetta, East Islip, both of N.Y.

[73] Assignee: A.T.F. Consolidated, Inc., Deer Park, N.Y.

[21] Appl. No.: 425,338

[22] Filed: Oct. 23, 1989

[51] Int. Cl.$^5$ .............................................. H05G 1/00
[52] U.S. Cl. ..................... 378/208; 378/20; 378/4
[58] Field of Search ...................... 250/363.03–363.05; 378/4, 20, 145, 208, 209, 205

[56] References Cited

U.S. PATENT DOCUMENTS

| | | | |
|---|---|---|---|
| 3,011,057 | 11/1961 | Anger | 250/71.5 |
| 3,432,660 | 3/1969 | Anger | 250/363.04 |
| 4,400,820 | 8/1983 | O'Dell et al. | 378/209 |
| 4,481,657 | 11/1984 | Larsson | 378/209 |
| 4,633,494 | 12/1986 | Klausz | 378/205 |
| 4,651,007 | 3/1987 | Perusek et al. | 250/363 S |
| 4,652,758 | 3/1987 | Barfod | 250/363 S |
| 4,674,107 | 6/1987 | Urban et al. | 378/98 |
| 4,698,506 | 10/1987 | Fujiki | 250/363 S |
| 4,702,257 | 10/1987 | Moriyama et al. | 378/4 |
| 4,779,858 | 10/1988 | Saussereau | 269/328 |
| 4,802,195 | 1/1989 | Wojcienchowski et al. | 378/208 |
| 4,891,833 | 1/1990 | Bernardi | 378/145 |

*Primary Examiner*—Edward P. Westin
*Assistant Examiner*—Kim-Kwok Chu
*Attorney, Agent, or Firm*—Larson and Taylor

[57] ABSTRACT

An emission tomography carousel system and method for use with a stationary radiation detector in Single Photon Emission Computer Tomography (SPECT) procedures is disclosed. In a preferred embodiment the carousel includes a patient platform having a seat and a tiltable, fiberglass composition back support, and includes two linear motion positioning tables and one rotary motion positioning table as part of a positionable mounting for moving the patient platform in three degrees of motion. A programmed computer controls the motion of the carousel about a predetermined locus of points. The method includes positioning the carousel in a "home" position, placing a patient in the carousel and manually positioning the patient platform to a desired close position with respect to a stationary radiation detector. The position is then recorded in the memory of a control computer and the procedure is repeated to obtain the desired number of radii of the patient's organ of interest to the detector. If the desired locus of points that the patient's organ is to traverse is a known geometrical figure (the most common of which is an ellipse), then a computer is used to calculate the remaining points. After "teaching" the computer the desired motion to be undertaken, the computer is activated and the computer automatically positions the patient in a large plurality of aspects with respect to the detector. However, in each aspect, the organ of interest is kept as close as possible to the center of the figure being circumscribed.

6 Claims, 11 Drawing Sheets

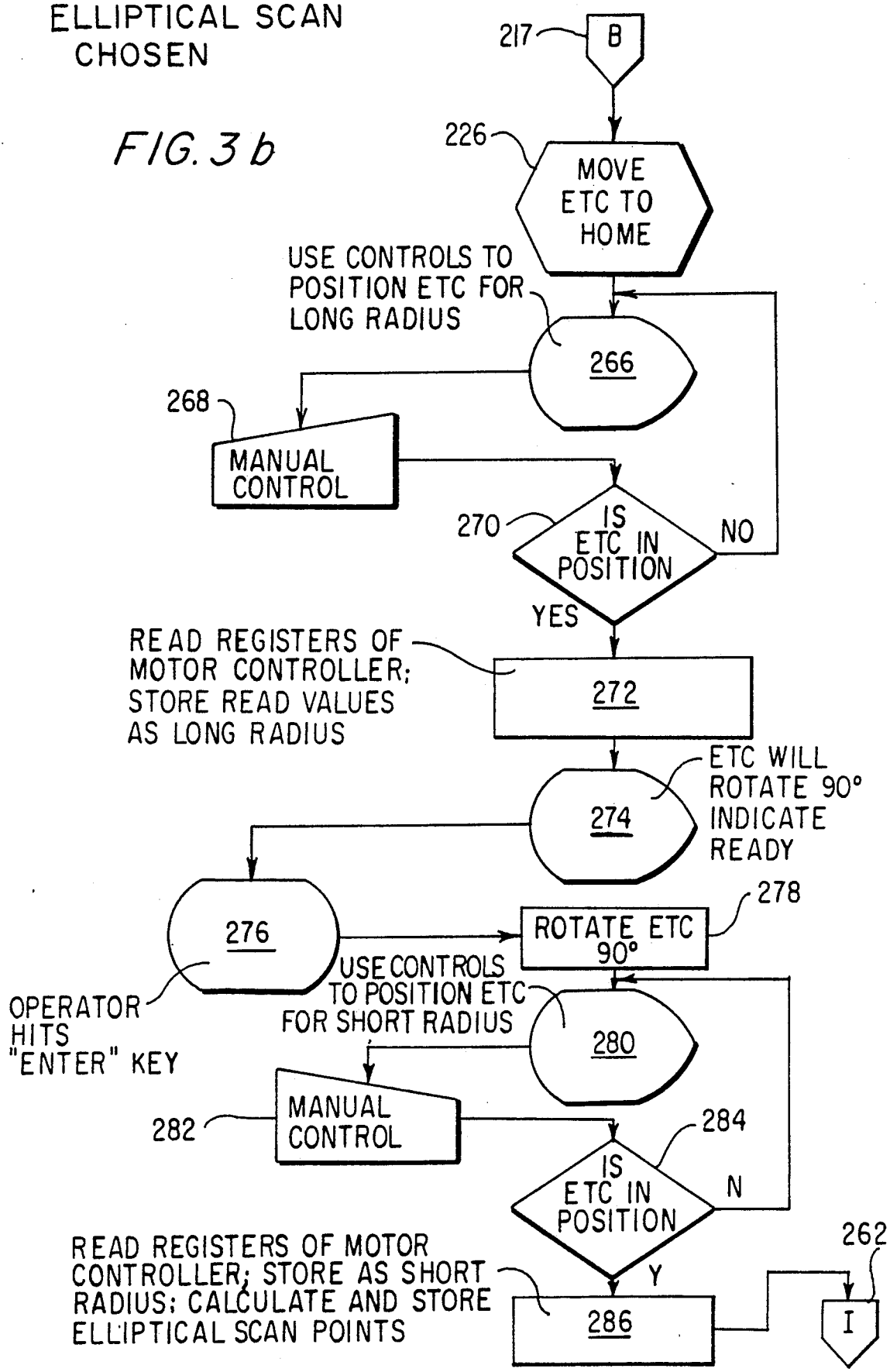
FIG. 3b — ELLIPTICAL SCAN CHOSEN

IRREGULAR SCAN CHOSEN

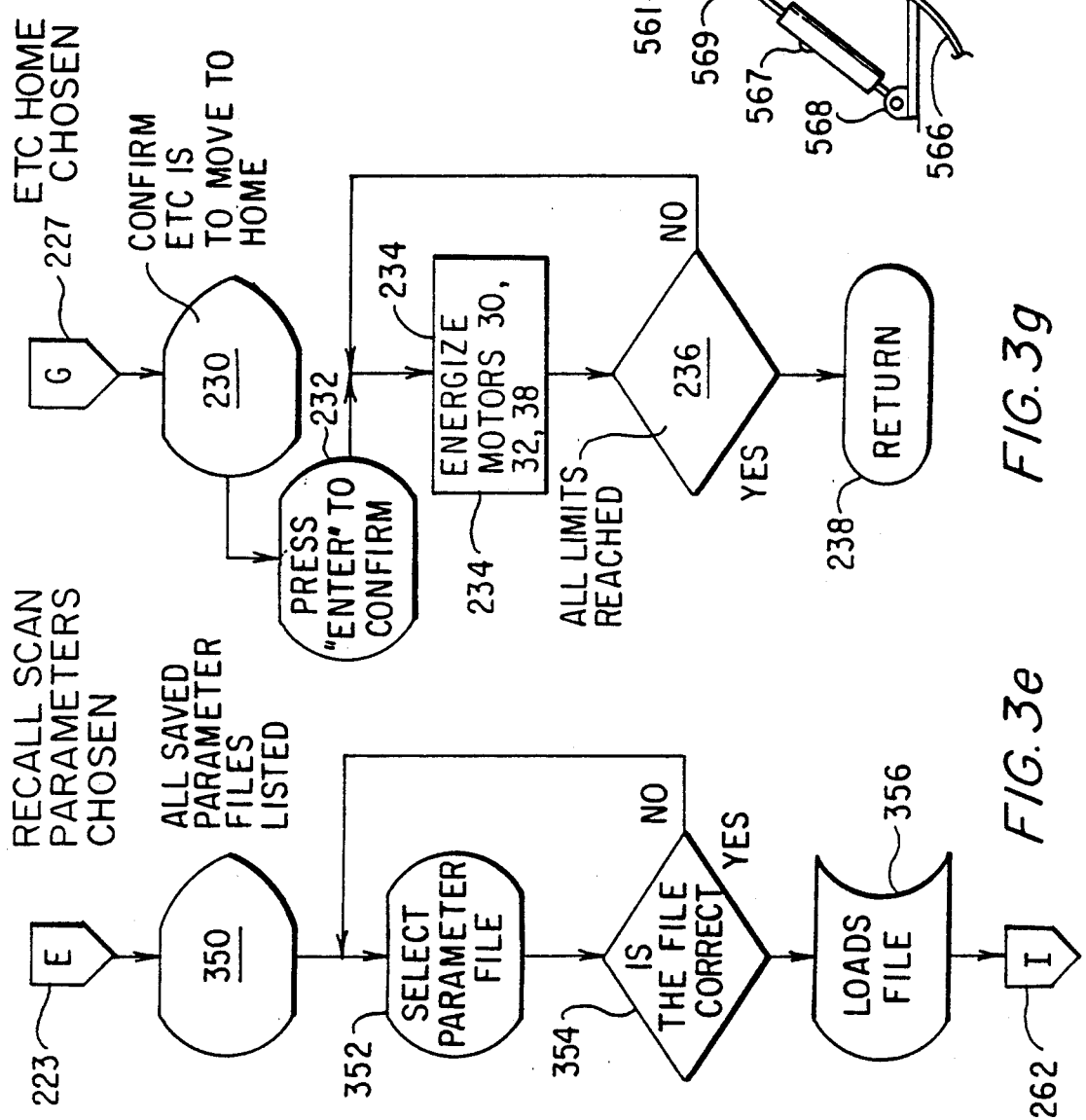

START SCAN CHOSEN

EMISSION TOMOGRAPHY CAROUSEL SYSTEM AND METHOD

RELATED DISCLOSURE DOCUMENT

A disclosure document related to the present application was filed on July 5, 1988, and assigned No. 199,862.

FIELD OF THE INVENTION

The present invention relates to the field of tomography in general, and more specifically relates to the field of emission tomography and S.P.E.C.T. or SPECT (Single Photon Emission Computer Tomography). In particular, the present invention relates to a system and method of utilizing a stationary radiation detector and a movable patient carousel for collecting the tomography data.

BACKGROUND OF THE INVENTION

Emission tomography is a field of medical diagnostic science in which a radiation detector is used for obtaining an image of the radiation distribution from a radioisotope within the body of a patient. A conventional computer program can use the received data to produce a "picture" in two dimensions of the radiation distribution of a section through a patient. Usually, the radioisotope is ingested into the patient either orally or by injection and is of the type that concentrates in the area of the body to be investigated. For example, certain isotopes tend to concentrate in a tumor, and certain isotopes concentrate in particular body parts (e.g. iodine isotopes concentrate in the thyroid gland). Once the isotopes are concentrated, the radioisotope detector is used to detect the radiation at various points about the body and then a computer is utilized to generate two dimensions depictions of the radiation concentration aligned along a selected axis at various points on that axis.

In order to detect the radiation at the various points, it is necessary to move the patient relative to the detector. Two Anger U.S. Pat. Nos. 3,432,660 and 3,011,057 disclose an early type of radiation image detector and a tomography carousel in which the patient moves relative to the detector.

However, in more recent emission tomography apparatuses, including gamma radiation camera SPECT systems, the scintillation camera head, or radioisotope detector, rotates around a patient positioned on a separate patient support. Several U.S. patents disclose tomography devices in which the detector orbits the patient. They include the Perusek et al U.S. Pat. No. 4,651,007 (disclosing an apparatus capable of circular and noncircular orbits with individual positioning of the detector and of the patient support table); and the Fujiki U.S. Pat. No. 4,698,506 and Barfod U.S. Pat. No. 4,652,758 (disclosing devices in which patient support is positionable with respect to an orbiting detector.

Any system in which the detector moves will suffer form undesirable detector motion and image degradation resulting from such motion. In addition, such detectors have an extremely high density and typically weigh 1 to 2 tons. Therefore maintaining the accuracy during the rotational motion requires an extremely expensive support and motion control systems. Nevertheless, such systems still suffer from a lack of concentricity and angular locatability. The other disadvantages of such systems are their high cost, huge size and mechanical repair problems. As the result of the cost and size, there are relatively few medical institutions that can afford to obtain and use the conventional, commercially available SPECT systems. Consequently, the highly diagnostic SPECT procedures are unavailable for a significantly large number of medical institutions.

One reason why the medical diagnostic apparatuses developed from the concept of a stationary detector disclosed in the aforementioned Anger patents to that of the movable detector disclosed in the other aforementioned patents is the lack of proper patient support provided in the former devices. Without such support, patient movement will add greatly to the inaccuracies thereof. Several U.S. patents disclose patient supports usable with radiation equipment. These patents include the Saussereau U.S. Pat. No. 4,779,858; the O'Dell et al U.S. Pat. No. 4,400,820; the Larsson U.S. Pat. No. 4,481,657; and the Urgan et al U.S. Pat. No. 4,674,107. Many of these patents merely disclose a patient table that has provision for immobilizing the patient and which is simply positionable relative to a radiation detector or radiation source.

There is therefore the need for an emission tomography carousel usable to perform SPECT which is relatively inexpensive, requires a minimal amount of space, is sturdy yet accurately positionable, and which is versatile in use for the various body organs that can be investigated.

SUMMARY OF THE INVENTION

The present invention is directed to an emission tomography carousel system and method and comprises and uses a stationary scintillation detector, sometimes called a gamma camera) and a very accurately positionable carousel having four degrees of motion relative to the detector. In a specific embodiment, a very accurate computerized motor control system moves the carousel in three of those degrees of motion. Such a system and method can keep the organ of interest within the image field of the detector and very close to the center of revolution during the movement of the patient, permit the use of a relatively small and inexpensive detector system, and can be utilized in a relatively small area. In addition to these advantages, the present invention also provides extremely good accuracy of angular placement and concentricity with excellent reproducibility of results. The present carousel system can be adapted for use with existing non-rotational detector systems to enable them to be used for SPECT imaging.

The present invention utilizes a carousel mounted on a supporting plate that is both rotational and translatable along orthogonal axes. A programmed computer is used to calculate the movement of the carousel about the detector so as to maintain the target area of the patient as close as possible to the detector and in the center of the field of the detector during such motion. The carousel incorporates support surfaces and attachment devices to maintain the portion of the patient being investigated in a motionless state.

BRIEF DESCRIPTION OF THE DRAWINGS

FIGS. 3a through 3h comprise flow charts of subroutines called by the computer program of FIG. 3.

FIG. 6 is a side elevational view of the reclinable carousel of FIG. 5.

DETAILED DESCRIPTION OF THE PREFERRED EMBODIMENTS

Figure 1:
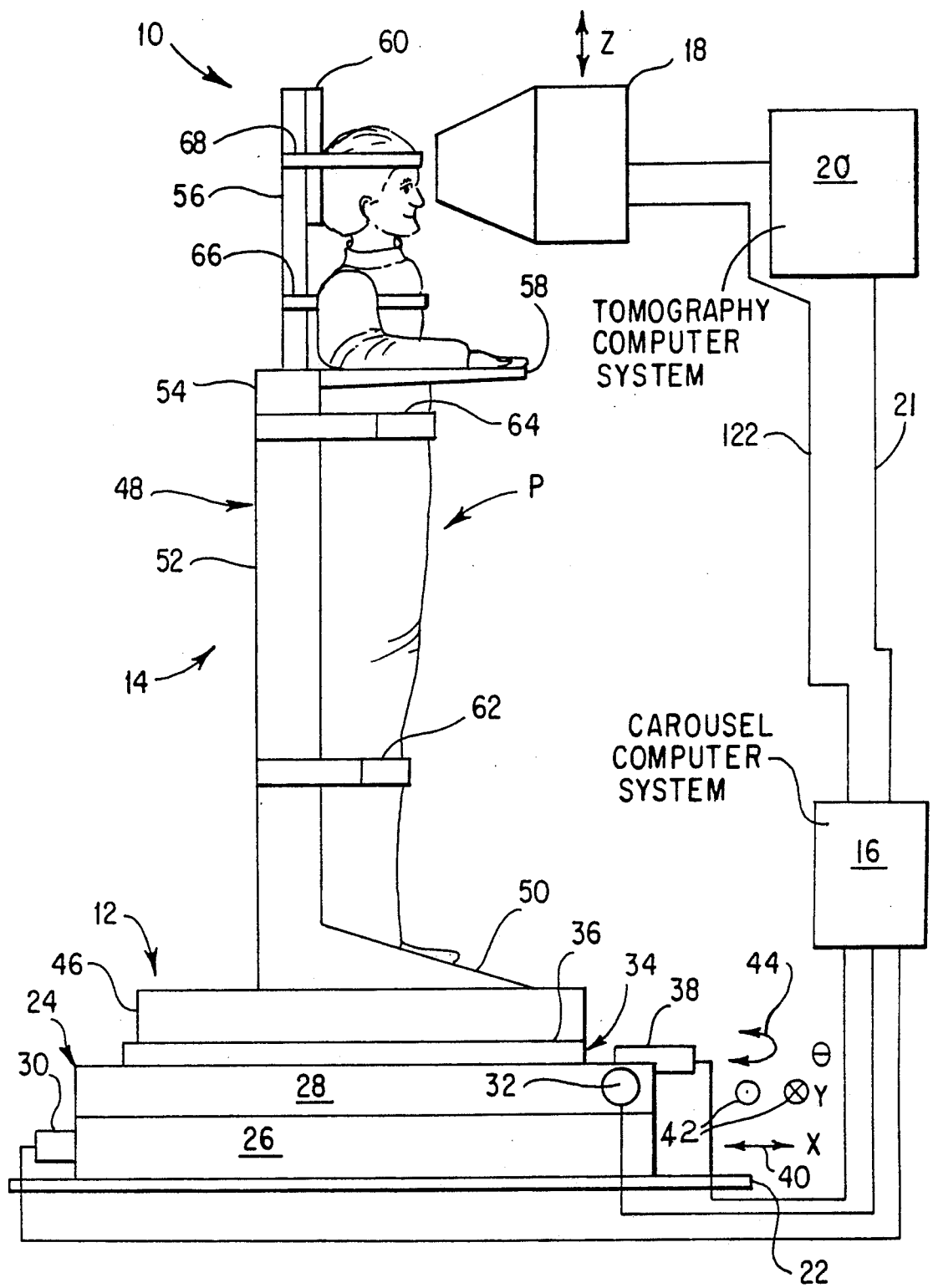
FIG. 1 is a front elevational, schematic view of a carousel support system for a standing patient.

With reference now to the figures, like elements have like numerals throughout the several views and similar elements have the same last two digits. With particular reference to FIG. 1, there is depicted a carousel 10 according to the present invention for a standing patient P. Carousel 10 is comprised of a translational and rotational positioning base 12 and a patient support 14 rigidly mounted to and movable by positioning base 12. The positioning of patient support 14 is accomplished with a programmed, conventional microcomputer system 16, which for example can be an AT model microcomputer. FIG. 1 also depicts a conventional gamma camera 18 connected to and controlled by a conventional emission tomography computer system 20. Tomography computer system 20 receives a status line enable signal, described below, from carousel computer system 16 on a connector 21. Gamma camera 18 is conventionally, rigidly mountable and vertically positionable on a stationary support platform (not shown). In FIG. 1, gamma camera 18 is shown in position for a SPECT brain scan.

Carousel positioning base 12 is comprised of a floor support plate 22 that is accurately positionable on the floor and which in turn supports and has mounted thereon a three degree of motion positioning platform 24. Positioning platform 24 is in turn comprised of a lower X-axis linear motion positioning table 26 rigidly mounted directly to support plate 22, and an upper Y-axis, open frame linear motion positioning table 28. Tables 26 and 28 have exemplary dimensions of a 21 inch (53.3 cm) square with a 7 inch (17.8 cm) travel in either direction from a center position at a straight line accuracy of 0.0002 inch (0.005 mm) per inch (2.54 cm) of travel. Point to point indexing of tables 26 and 28 is obtained by a side mounted leadscrew assembly (not shown) driven by corresponding computer compatible conventional stepping motors 30 and 32, respectively, that are connected to and controlled by carousel computer system 16. Positioning platform 24 is also comprised of a rotary indexing table 34 mounted within and movable with table 28. Table 34 includes a rotary top 36 that is capable of being rotated at least 360 degree in either direction. Table 34 is rotated by a computer compatible conventional stepping motor 38 that drives a precision worm gear drive capable of providing precise and accurate rotational positioning with no backlash with an accuracy of at least 6 seconds of arc.

Thus, positioning platform 24 can accurately move patient support 14 in any geometrical pattern about floor plate 22 and accurately position a patient P mounted therein in any horizontal aspect with respect to the stationary gamma camera 18. These degrees of freedom and movement are depicted by arrow 40 for the X - axis, arrows 42 for the Y - axis, and arrow 44 for the rotational angle Theta.

Rigidly mounted to rotary top 36 of table 34, such as with bolts (not shown), is a patient support plate 46. Patient support plate 46, in turn, rigidly supports a patient support frame 48 that is comprised of a base 50 and a vertical, telescoping post 52 rigidly mounted to base 50 and having a lower section 52 and an upper section 54. Attached to the top of lower section 52 and extending perpendicularly therefrom is a patient arm support 58. Arm support 58 can be slidably mounted onto lower section 52 so as to accommodate patients of different body sizes. Attached to the top of upper section 56 is a padded cushion 60 for receiving the head of patient P. Patient P is rigidly held in a non-movable condition on patient support 14 by a plurality of restraining straps 62, 64, 66 and 68.

Figure 2:
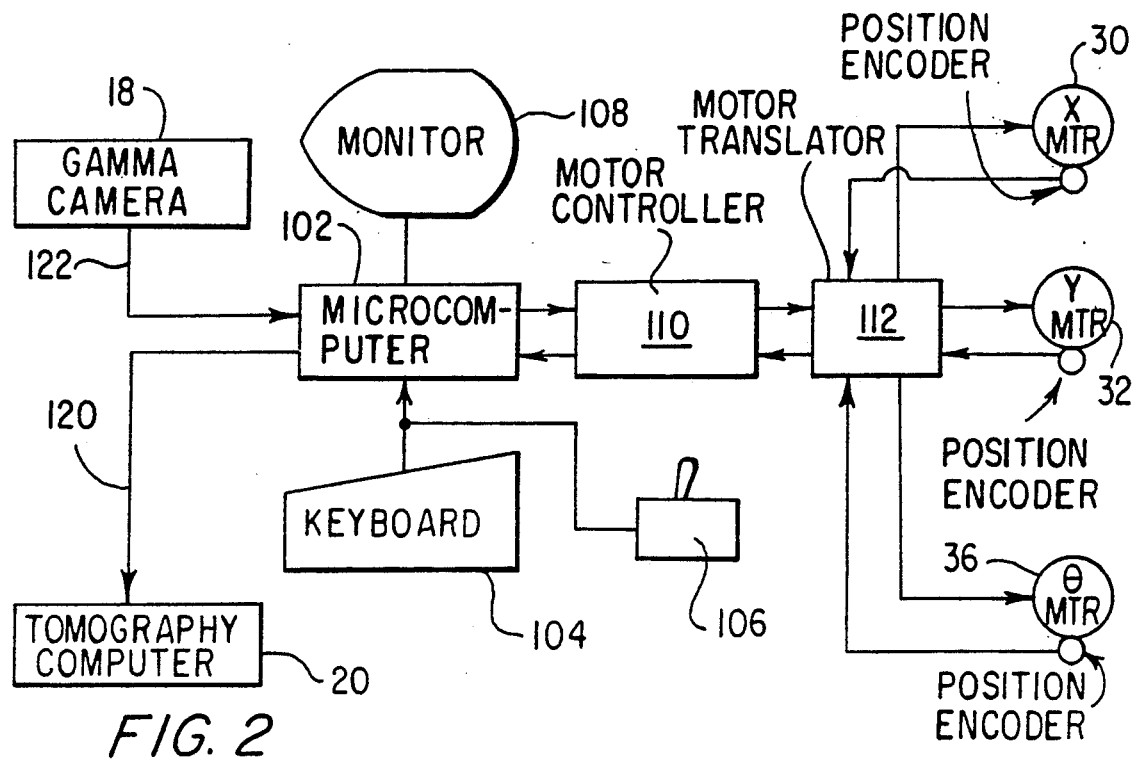
FIG. 2 is a general electrical schematic diagram of the computerized carousel control system.

With reference now to FIG. 2, a more detailed block diagram of carousel computer system 16 and its interconnections to the other system components are depicted. Computer system 16 is comprised of a conventional microcomputer 102, an input device, such as a keyboard 104 and/or a joystick 106, and a monitor 108. Connected to the output of computer 102 is a conventional motor controller 110. Motor controller is preferably of the digital computer controlled type such as the PCX series manufactured by Oregon Micro Systems, Inc. of Beaverton, Oreg.

The PCX series motor controller is an intelligent motion controller that controls up to 6 axes in a board that fits in a slot of a PC/XT/AT IBM or compatible microcomputer. Each axis has a separate command queue thereby allowing microcomputer 102 to transfer a command string, then proceed to other tasks, and then be interrupted to coordinate the motion process with other activities. The PCX series generates step and direction pulses for control of conventional step motor drivers with a high resolution microstepping of 50,000 steps per revolution with a standard 200 step per revolution stepping motor. A velocity streaming mode allows an arbitrary move contour developed by microcomputer 102. Further, the PCX series permits incremental encoder feedback for precise positioning. The PCX motor controller uses a published assembly language programming commands to set specifications, issue system control commands, set move specifications and executions, cooperate with encoder signals, and general programming commands (such as loop commands to allow move sequences to be repeated). As a simplistic example, the PCX programming language to move simultaneously a distance of 1,000,000 pulses on the X axis and the Y-axis, each move with a velocity of 400,000 pulses per second at a peak acceleration of 500,000 pulses per second per second, is:

| AA | Axis All—a context switch to the synchronized mode |
|---|---|
| VL400000,400000; | VeLocity command |
| AC500000,500000 | ACceleration command |
| MR1000000,MR1000000 | Move Relative commands |
| GO | the execute command |

The programming commands can be issued directly from keyboard 104, or more usually, written in advance, stored in microcomputer 102, and then executed upon a command issued from keyboard 104. Alternative, operator issued signals can be provided by joystick 106 to position patient support 14 on a real time basis. One purpose of using the joystick would be to quickly define the parameters of a circular, elliptical or irregular carousel movement, after which microcomputer 102 programmed with conventional, commercially available software can perform the necessary calculations and provide the commands to motor controller 110.

Signals from motor controller 110 are transmitted to a conventional motor translator 112 which translates the signals into the appropriate number of step command pulses for the appropriate direction for the particular one or more of motors 30, 32 and 34. Each one of motors 30, 32, and 34 have corresponding position encoders 114, 116 and 118 which constantly provide signals representative of the actual, current position of the corresponding motor or the actual, current position of the corresponding table, depending upon the particular embodiment of the invention. As depicted in FIG. 2, the signals from position encoders 114, 116 and 118 are sent to microcomputer 102 through motor translator 112 and motor controller 110.

As also shown in FIG. 1, microcomputer 102 also provides and receives other communication signals from the system components. As mentioned above a status signal is sent to tomography computer system 20 on line 21. In one embodiment, status signal is simply a high or a low signal representative of when patient support 14 is moving or not moving, respectively. In addition, a camera contact signal is received by microcomputer 102 from gamma camera 18 on line 122. In a preferred embodiment of the invention, gamma camera has a conventional "skin" that is pressure sensitive such that any pressure anywhere on the skin provides a contact signal. The contact signal received on line 122 indicates that either the patient has come into contact with gamma camera 18 or that some other impermissible contact with gamma camera 18 has taken place.

In other embodiments, motor controller 110 incorporates the functions of motor translator 112 and a dedicated microcomputer 102 incorporates the functions of both.

Figure 3:
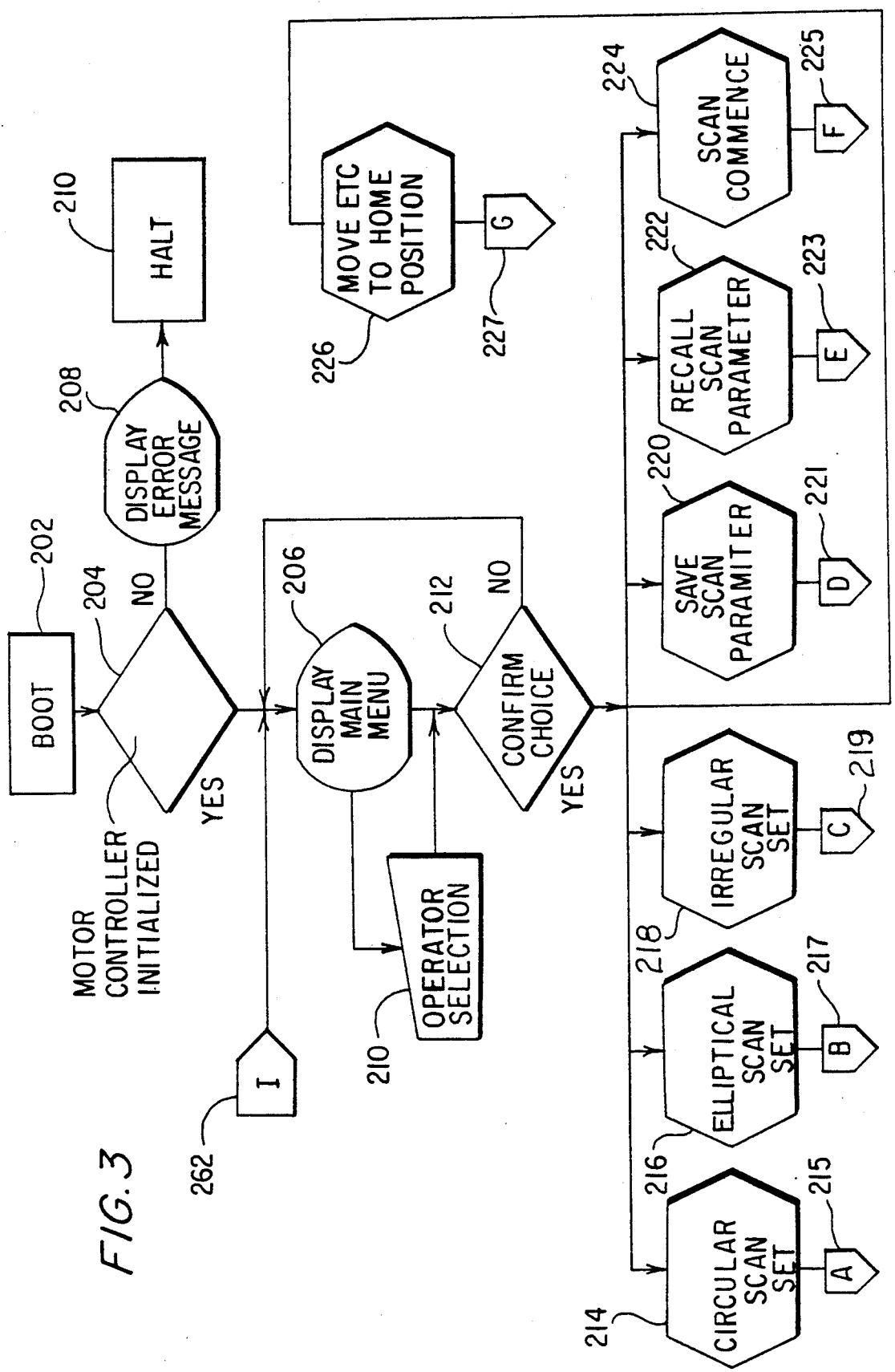
FIG. 3 is a flow chart of a computer program for operating the tomography carousel system.

Reference is now made to FIG. 3 where the program flow is depicted of the computer program used by microcomputer 102. FIG 3 and FIGS. 3a through 3f use conventional computer program flow chart symbols. The program steps of the computer program are interchangeably referred to herein by the symbol name (e.g. processing box 202 and decision diamond 206) and/or by the program step being carried out (e.g. boot step or boot routine 202).

When power to microcomputer 102 is turned on, a boot routine, represented by processing box 202, is run. Boot routine 202 is conventional and tests microcomputer 102 for proper operation and initializes motor controller 110. The initialization of controller includes resetting all controller registers and testing the operation of the controller system pursuant to the setup procedure of the manufacturer. Boot routine 202 also sets the "Esc" key on keyboard 104 as the interrupt key, sometimes called the hotkey and described hereinbelow with respect to FIG. 3g.

Upon completion of boot routine 202, the program flow proceeds to check in decision box 204 that motor controller 110 has actually been initialized. This is done by reading the registers of the controller and checking that they have all been set to zero. If such initialization has occurred, the program branches to the main menu display box 206. If there has been a problem and motor controller 110 does not indicate that it has been initialized, the program branches to error display box 208 where an error message is displayed on monitor 108, and then the program halts, as indicated by processing box 210.

As soon as the operator makes a selection, as indicated by input box 210, the program first checks in decision box 212 to ensure that the input selection was an allowable choice (i.e. was one of the options presented) and then displays an appropriate message on monitor 108 asking the operator to confirm the choice by pressing the "Enter" key on keyboard 104. If the selection was not an allowable choice, the program returns to main menu display 206. When the "Enter" key is depressed, the program calls the selected subroutine through its corresponding offpage connector. The subroutines and their corresponding offpage connectors are:

A. Circular Scan Set subroutine 214 and offpage connector 215;
B. Elliptical Scan Set subroutine 216 and offpage connector 217;
C. Irregular Scan Set subroutine 218 and offpage connector 219;
D. Save Scan Parameters subroutine 220 and offpage connector 221;
E. Recall Scan Parameters subroutine 222 and offpage connector 223; and
F. Scan Commence Subroutine 224 and offpage connector 225.
G. Move ETC To "Home" subroutine 226 and offpage connector 227.

As soon as the operator selects the desired subroutine, the program will call and commence executing that subroutine. The first step for all of the subroutines, except for the Save and Recall Scan subroutines 220 and 222, is to move patient platform 14 (sometimes called ETC for Emission Tomography Carousel herein and in the drawings) to the "HOME" position. Therefore the Home subroutine 226 will be discussed first.

The "home" position of patient support 14 is at a predetermined point (x,y) on floor plate 22 with patient support 14 being rotated to a predetermined angle Theta. For simplification of procedures and for ease of performing the maneuver, the home position has been selected as that position that is as far away from gamma camera 18 as possible to permit easy movement of a patient into and out of patient frame 48. This position puts all three tables 26, 28 and 34 into their stops where limit switches (not shown) deenergize their respective motors and reset respective status registers (not shown) of motor controller 110. The use of the limit switches to define when patient support 14 is in the Home position provides a high accuracy and a high repeatability factor. In a preferred embodiment, patient support 14 is rotated such that the back of the head of patient P is towards gamma camera 18. See, for example, FIG. 4g. For the purpose of convention, the home position has been designated (0,0,0°), where the variable values are (x,y,Theta). These values respectively represent the relative longitudinal distance "x", the relative transverse distance "y", and the relative angle of rotation Theta.

The particular absolute location of the home position can be at any point within the floor area of movement of patient support 14. In addition, the home position can be the same for every scan for the sake of consistency, as it is in the present embodiment, or the absolute home position can vary according to the scan to be performed.

With reference to FIG. 3g, when the program enters Home subroutine 226 through offpage connector 227, it first requests in display box 230 a confirmation from the operator that patient support 14 is to be moved to the Home position. When the operator confirms the movement in keying operation box 23 by hitting the Enter key, the program enters processing box 234 where it provides the necessary output signals to motors 30, 32 and 38 to move patient support 14 in the correct X, Y and Theta directions. During this movement, the program in decision box 236 monitors the status registers (not shown) of motor controller 110 to determine if they have been reset, thereby indicating that the limit switches have been activated and has reset the registers. As soon as the program determines that the home position has been reached in decision diamond 236, it branches back through terminal 238 to that point in the main program from which it came.

The operational selections of main menu display 206 will now be explained. If the operator selects circular scan set subroutine 214, depicted in FIG. 3a, the operator has decided to use a circular scan to take the SPECT. A circular scan set would be used to record the necessary parameters to have patient support 14 circumscribe a circle when the scan is run. A circle scan would be used for those circular portions of the body, usually the thyroid in the neck or the stomach for some overweight patients. To determine a circle, the center of which is always the center of patient support 14 and the circumference of which always abuts gamma camera 18, only one point need be determined. During initial set up of the carousel system, computer will have been loaded with certain parameters, such as the offset from the geometrical center of patient support 14 to the Home position and the number of degrees of rotation of a patient between shots taken by gamma camera 18. Once the one location is provided to microcomputer 102, the aforementioned commercially available computer program determines all of the other points on the circumference of the circle spaced the predetermined number of degrees apart, usually three.

When the operator hits the key to select the circular scan set (for example the letter "A") and confirms the selection by hitting "Enter" on keyboard 104, the program branches to subroutine 214 through offpage connector 215. The first step in circular scan set subroutine is for the program to call Home subroutine 226 to move patient support 14 to the "home position".

Once patient support 14 is at the home position, the program proceeds to display box 254 where the operator is asked to take manual control of the movement of patient support 14 and to position it for the first position for scanning a circle. Usually at this point the operator will have patient P mount patient support 14 and strap the patient in using straps 62, 64, 66 and 68 as necessary. The operator then positions patient support 14, as indicated by input box 256, using either appropriate keys of keyboard 104, such as the cursor keys, or with joystick 106. The program then awaits an indication from the operator, which is pressing the Enter key on keyboard 104, that patient support 14 is at the desired position. As mentioned above, this is the position which will define the desired point on the circumference of a circle to be scanned during scan subroutine 224, and is indicated by decision box 238. While awaiting receipt of the operator signal, the program loops back to display box 254. When the operator has signified that patient support 14 has been properly positioned, the program proceeds to a processing box 260 and reads the registers of motor controller 110, stores the positional information in memory, and calculates and stores the remaining points on the circumference of a circle to be scanned. The program then branches back to main menu display 206 through an offpage connector 262.

Figure 4A:
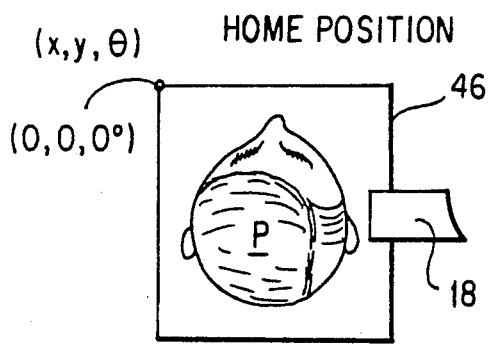
FIG. 4 is a series of eight diagrammatic figures labeled "a" through "h" depicting the relative movement between a patient area of interest, the brain, and a stationary isotopic detector.
Figure 4B:
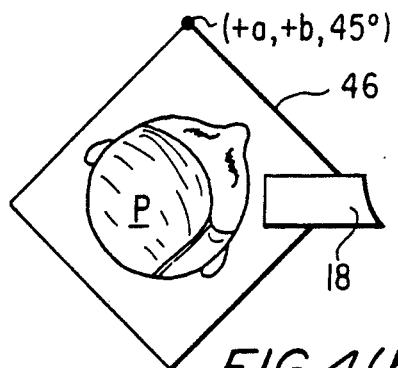
Figure 4C:
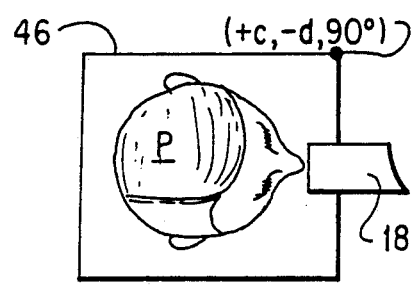
Figure 4D:
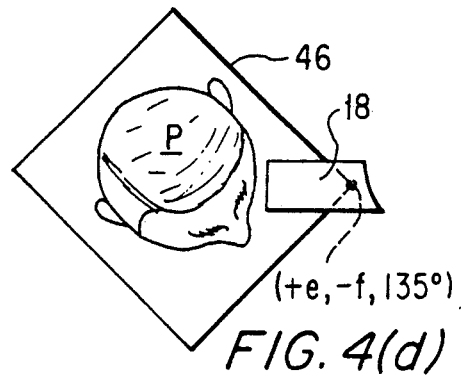
Figure 4E:
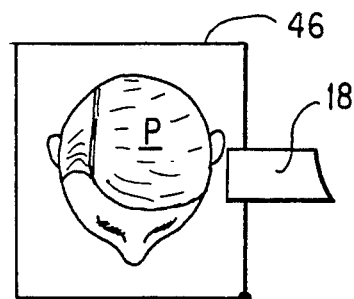
Figure 4F:
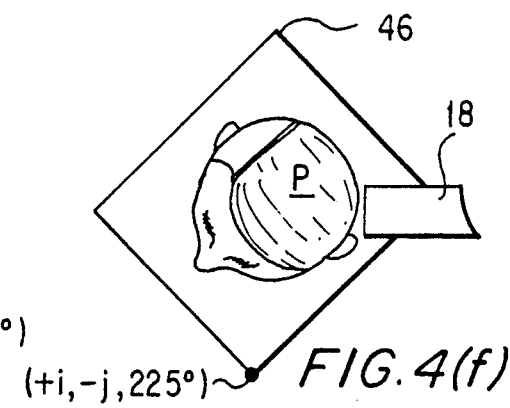
Figure 4G:
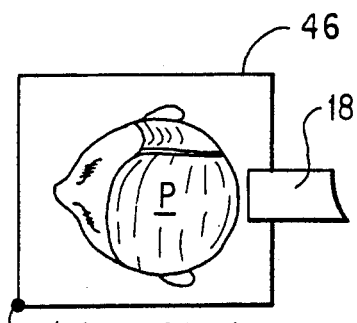
Figure 4H:
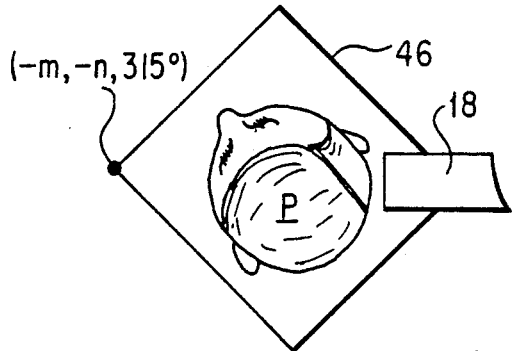

If the operator selects elliptical scan subroutine 216, depicted in FIG. 3b, the program branches thereto through offpage connector 217. After calling Home subroutine 226 and positioning patient support 14 to the "home position", the program proceeds to display box 266 where the operator is asked to take manual control of the movement of patient support 14 and to position it for the first position for identifying the long radius of the ellipse. For a brain scan, this position would be that depicted in FIG. 1 and FIG. 4c or 4g, and the ellipse is the shape of the patient's head. The operator then positions patient support 14, as indicated by an input box 268. As indicated by a decision box 270, the program loops back to display box 266 until the operator indicates that the desired position of patient support 14 has been reached. The program then proceeds to a processing box 272 where it reads the registers of motor controller 110, and stores the read values as the long radius of the ellipse. The program then continues to a display box 274 where the operator is advised to indicate when he or she is ready for patient support 14 to be rotated 90 degrees. When the operator has provided a signal to the program, as indicated in a keying operation box 276, the program proceeds to a processing box 278 where it accomplishes this rotation. The program then proceeds to a display box 280 where the operator is requested to take manual control and position patient support 14 for the short radius of the ellipse. For the aforementioned brain scan, this position is depicted in FIG. 4a or 4e. The operator then positions patient support 14, as indicated by an input box 282. Once again, as indicated by a decision box 284, the program waits for the indication from the operator that patient support 14 has been properly positioned by looping back to display box 280. When the operator has pressed the "Enter" key on keyboard 104 to indicate that patient support 14 has been properly positioned, the program proceeds to a processing box 286. In processing box 286 the program again reads the registers of motor controller 110, and stores these values as the short radius of the ellipse. The program then uses commercially available software to use the obtained short and long radii to calculate the points on the circumference of the ellipse to be traversed by patient support 14. The separation between points can be the usually chosen angle of three degrees. The program then branches back through offpage connector 262 to main menu display 206. The positions of patient support 14 when it is moved during the running of an elliptical scan (subroutine 224) is depicted in FIG. 4 for eight cardinal points of the 64 points of an average 360° scan.

Figures 3A, 3D:
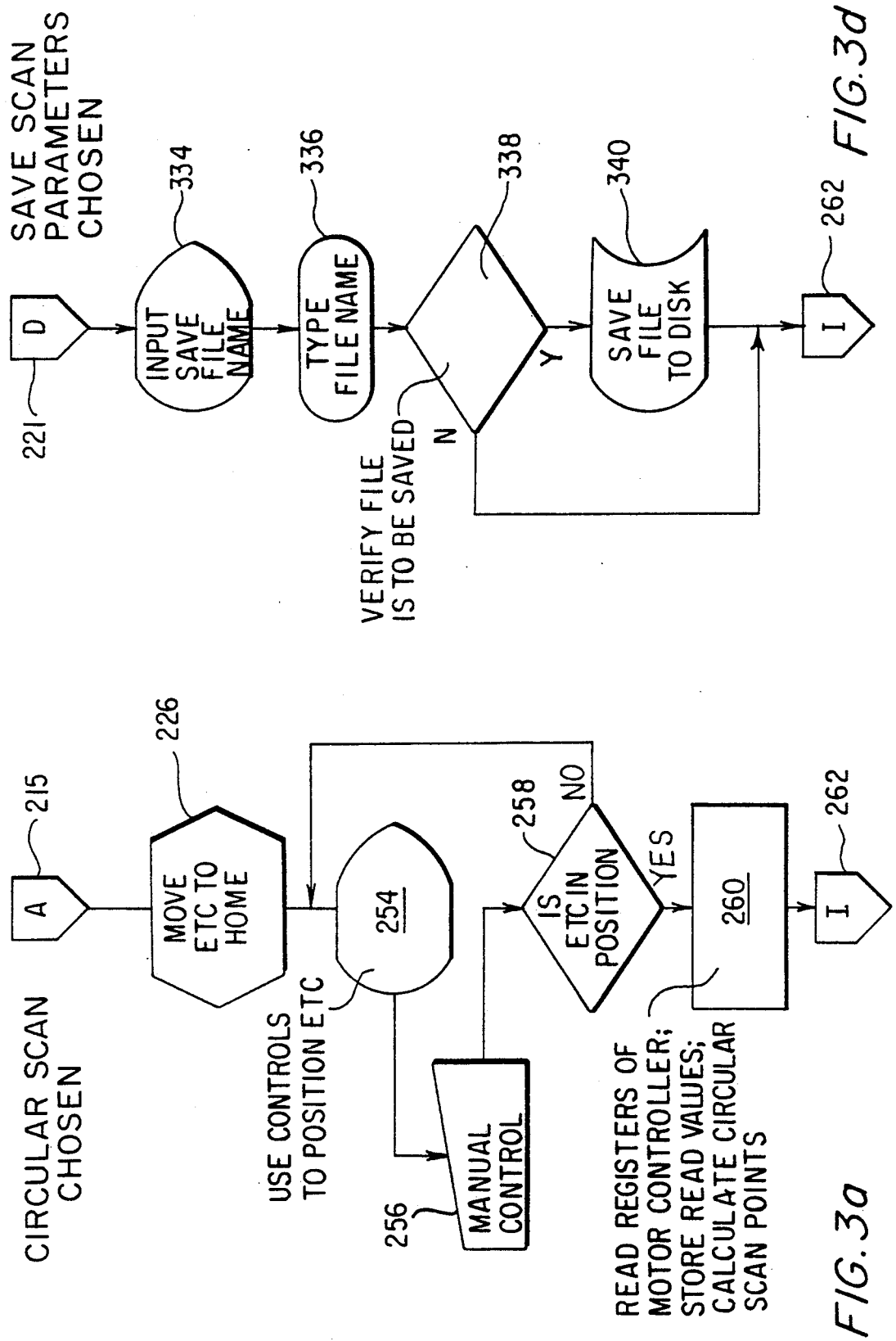
Figure 3C:
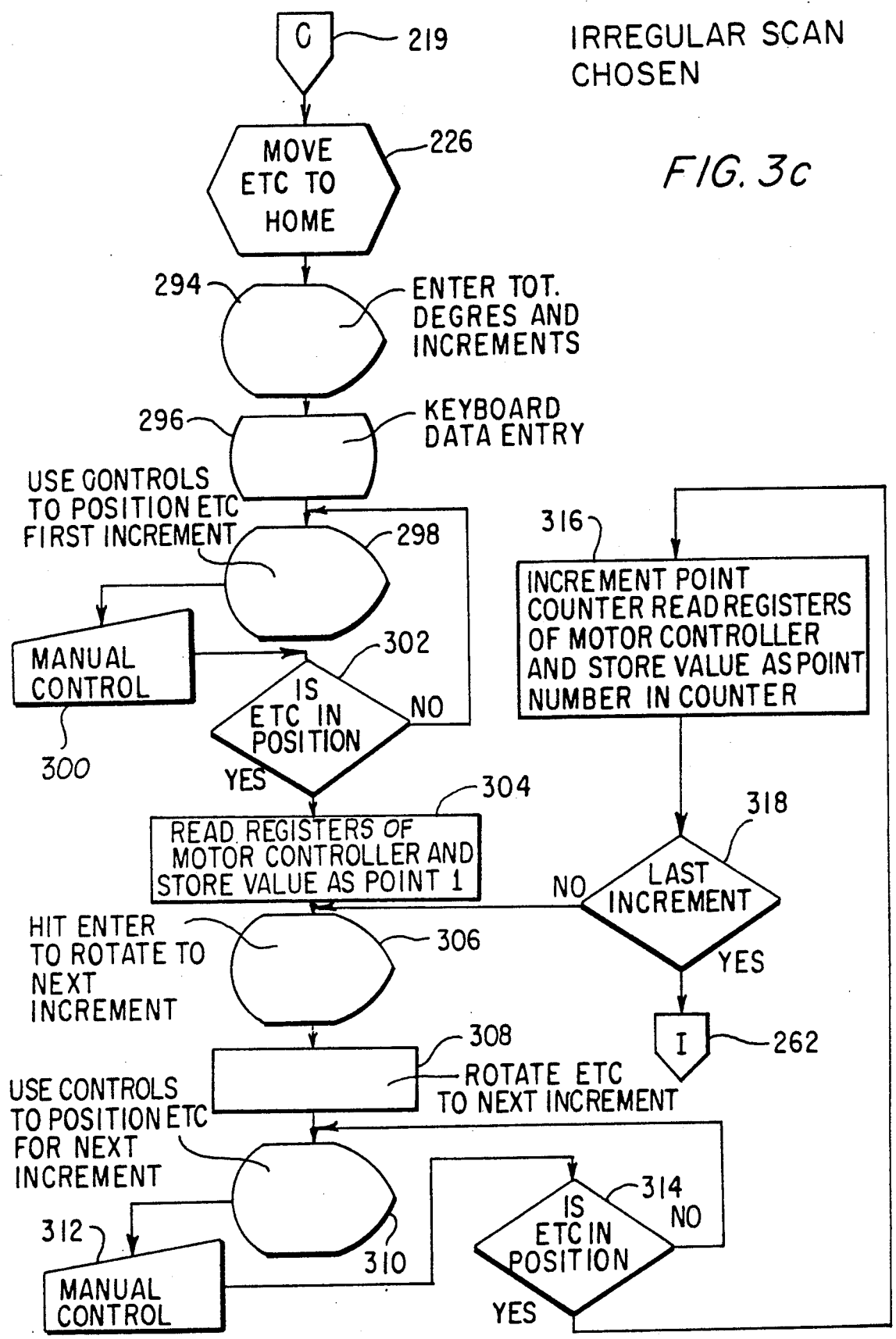
Figure 3F:
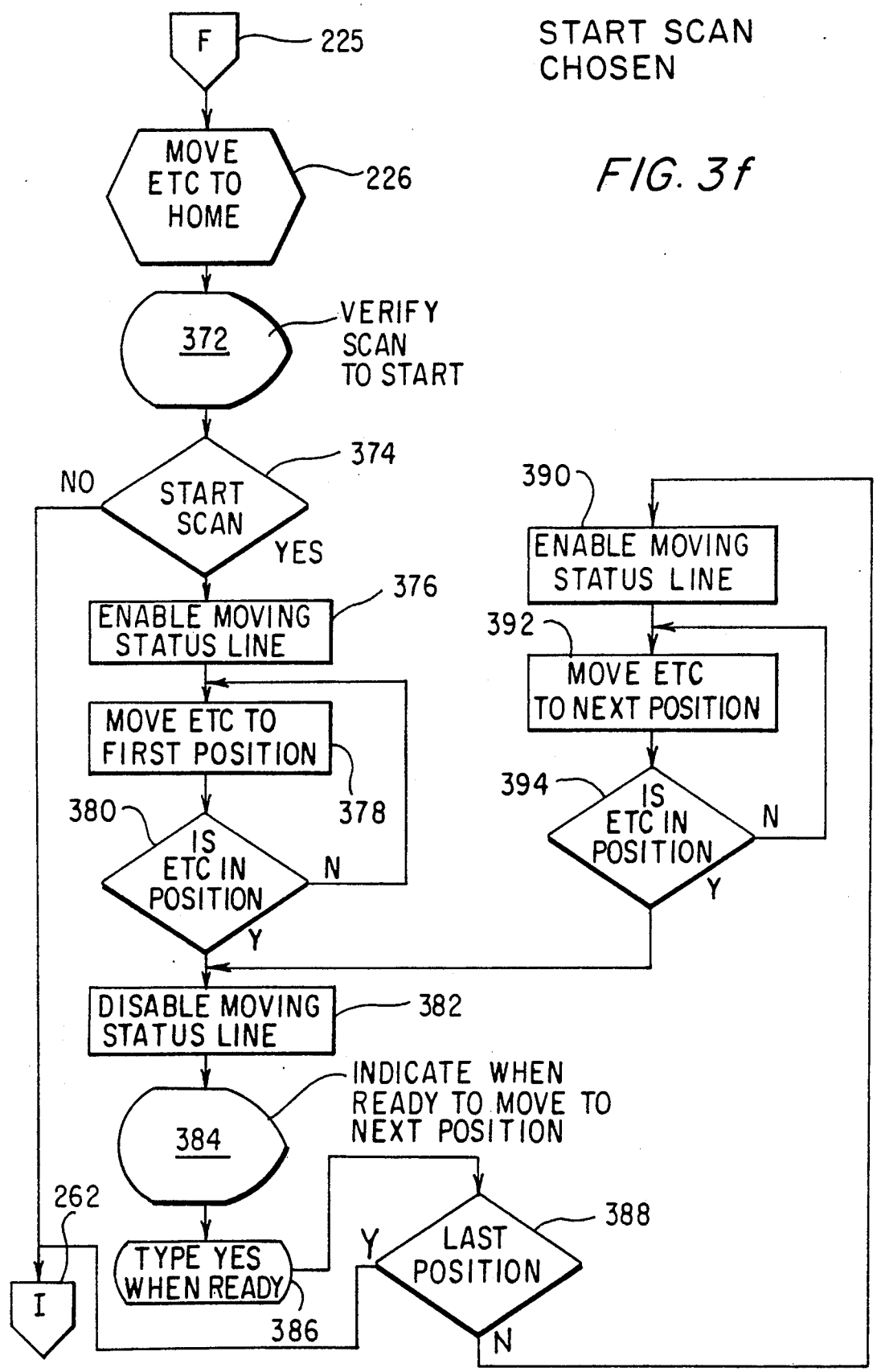
Figure 3H:
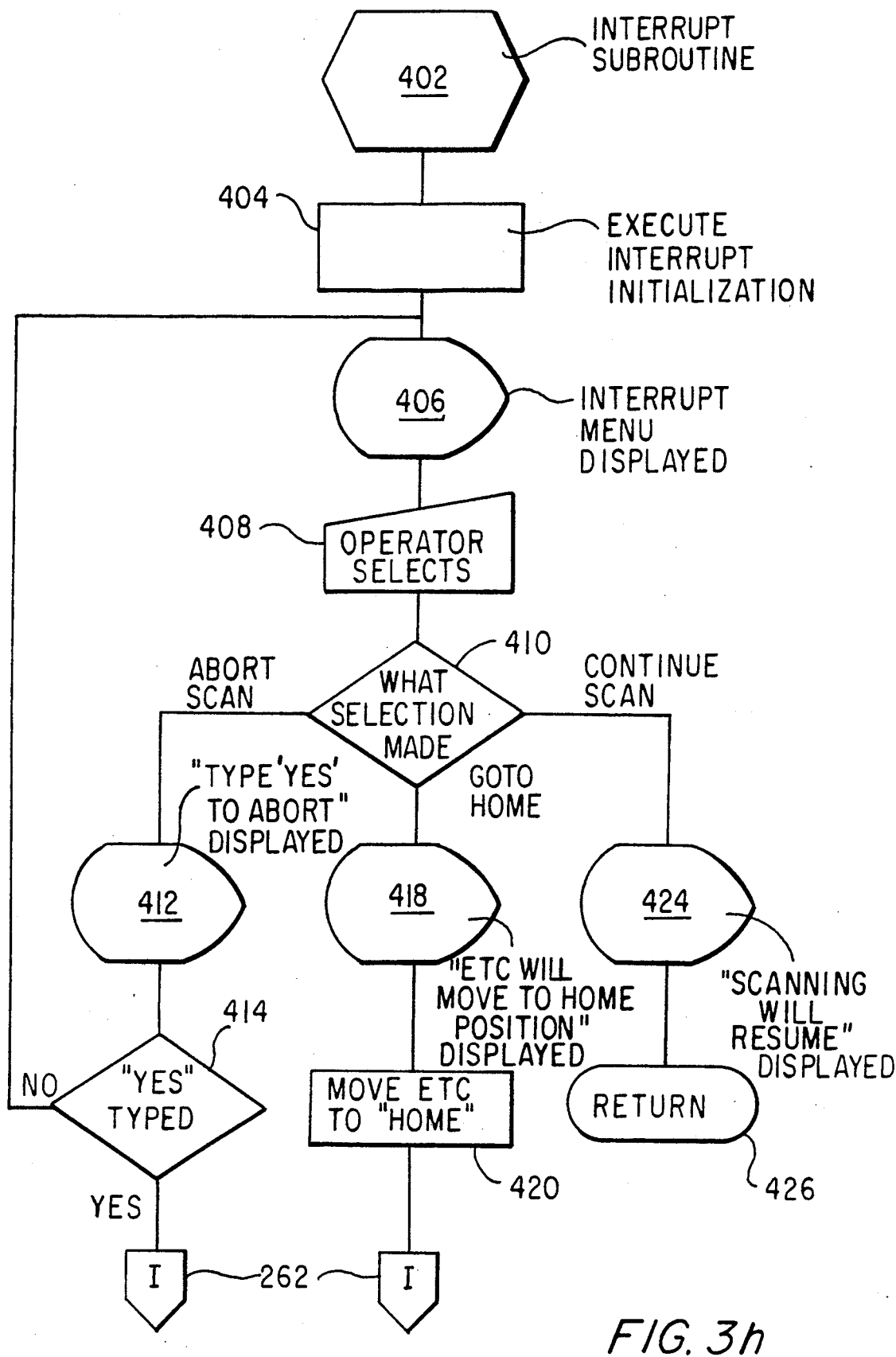

When the irregular scan set option is selected, the program proceeds as depicted in FIG. 3c. After calling Home subroutine 226 and positioning patient support 14 to the "home position", the program proceeds to a display box 294 where the operator is asked to enter the total rotation in degrees and the number of increments for the scan (i.e. how many shots will be taken by gamma camera 18).

Although the number of shots that are taken are a function of the protocols of SPECT and the particular organ being investigated, as mentioned above, the average rotational increment between shots for all scans is between 2.7 and 5.6 degrees (i.e. 64 steps in 360 degrees). The operator loads in these values in a keying operation box 296 using keyboard 104. The operator is then asked in a display box 298 to position patient support 14 to the first position. As in the other scans, the operator enters in the control signals in an input box 300, and in a decision box 302 the program asks the operator to hit "Enter" when patient support 14 is properly positioned. While the program waits for the input from the operator, it loops back to display box 298.

When the operator input is received, the program proceeds to a processing box 304. There the program reads the registers of motor controller 110 and stores those values as an identifiable number, which for the purposes of this example is denoted point 1. The program then proceeds to ask the operator to indicate when the patient support 14 is ready to be rotated to the next position, as indicated in a display box 306. This rotation is accomplished in a processing box 308. Again at the conclusion of the movement, the operator is asked in a display box 310 to move patient support 14 to the next increment. The manual control is depicted at an input box 312.

The program then again asks in a decision diamond 314 if the patient support 14 is in position. If patient support 14 is not in position, the program loops back to the input side of display box 310. If it is in the proper position, then the program proceeds to a processing box 316 where the program increments the point counter, the identity of the point being recorded, reads the motor controller registers, and stores the value as the point number in the point counter. From processing box 316 the program asks in a decision box 318 whether the previous increment was the last one. If not, the program loops back through display box 306. If the last position has been reached, the program branches back to main menu display 206 through offpage connector 262.

Once a scan has been set, that is all of the points to which patient support 14 will move have been determined either by actual positioning (e.g. for irregular scan settings) or by calculations using conventional software once certain locations have been determined (i.e. the major and minor radii for the case of elliptical rotations and the radius for circular rotations), the operator may then choose subroutine 220 to save the data.

The save subroutine is depicted in FIG. 3d, and it begins in a display box 334 where the operator is asked to supply the file name under which it is to be filed. The operator then uses keyboard 104 to supply the file name, as indicated in keying operation box 336. The program then asks again, in decision diamond 338, if the file is to be saved. If the operator answers affirmatively, the program saves the file to disk, as indicated in on-line storage box 340. From both storage box 340 and from decision diamond 338 when the file is not to be saved, the program returns to the main menu display 206 of the main program through offpage connector 262.

In order to run the scan program, a data scan file must have just been created, as is the normal case, or has been previously saved, as is sometimes the case if a repeat scan is to be performed within a short period of time. FIG. 3e depicts the flow of subroutine 222 to retrieve a file previously saved during the running of subroutine 220.

When the operator selects subroutine 222 at the main menu for recall scan parameters, the program enters the subroutine through offpage connector 223 and proceeds to a display box 350. In display box 350, the program prints all of the previously saved files to monitor 108.

The operator then selects the file to be retrieved in keying operation box 352. The program then requires the operator to confirm that the selected file is the one that the operator wants, indicated in a decision box 354. If the identified file is incorrect, the program loops back to keying operation box 352. If the operator indicates (e.g. by typing a "Y" on keyboard 104) that the selected file is the desired file, the program proceeds to memory retrieval box 356 where the file is loaded into the active memory of microcomputer 102. The program then returns to main menu display 206 through offpage connector 262.

As mentioned above, in most situations, after the program has set the desired scan, the scan will be immediately run. To run the scan, the file must be loaded into microcomputer 102 if the file was not just created. When the operator selects the Commence Scan subroutine 224, the program branches through offpage connector 225 and performs the Home subroutine 226, as described above. After patient support 14 is in the home position, the program requires the operator to verify that the scan is to start by displaying a message on monitor 108 as indicated in a display box 373 and as queried in a decision box 374. If the operator indicates that the scan is not to commence, the program returns to the main menu display 206 through3rough offpage connector 262.

However, if the operator confirms that the scan is to start, the program proceeds to a processing box 376 where it sends an enabling signal over moving status line 21 (FIG. 1, connected between carousel computer system 16 and tomography computer system 20. This signal tells system 20 that carousel 10 is moving, that no good data can be received, and thus that the gamma camera must be deactivated. From processing box 276 the program goes to a processing box 378 where it moves patient support 14 to the first position. The program then remains in a loop between a decision box 380 and processing box 378 until the operator presses the "Enter" key to indicate that patient support 14 is in position. Upon receipt of the operator's "go ahead" signal, the program proceeds to a processing box 382 where it disables moving status line 21, thereby permitting tomography computer system 20 to take over, active gamma camera 18, and take the first picture.

The program, in the meantime, enters a display box 384 where the operator is advised to indicate when tomography computer system 20 is done and carousel computer system 16 can take over. This indication is provided by the operator to the program by typing in a keying operation box 386 the word "yes" on keyboard 104. The program thereupon checks to see if the previous position was the last position in a decision box 388. If it is the last position, the program branches to main menu display 206 through offpage connector 262. If the previous position was not the last position, then the program branches to a processing box 390 where moving status line 21 is enabled, goes to processing box 392 where it moves patient support 14 to the next position, and finally to a decision box 394. The program loops between decision box 394 and processing box 392 until the operator signifies that patient support 14 is in position. At this time the program branches back to processing box 382 to disable moving status line 21 and begin the process again.

With reference now to FIG. 3g, an interrupt subroutine 402, referred to above, is depicted. Interrupt subroutine 402 is called by pressing the hotkey (i.e. the "Esc" key) on keyboard 104. When called, interrupt subroutine 402 begins in processing box 404 where the interrupt initialization is performed. Interrupt initialization 404 saves the appropriate data, clears the screen of monitor 108, and displays an interrupt menu 406. Interrupt menu 406 gives the operator the choice of sending patient support 14 to the "Home" position; continuing a scan that may have been in progress, or aborting a scan that has been in progress. The selection of the operator is indicated by input box 408 and the program determines that selection in decision diamond 410. If the operator chooses the abort scan option, the program branches to display box 412 where the operator is given a warning on monitor 108 (FIG. 2) and asked to confirm the abort selection. Upon receiving the operator input of "yes", as determined in decision diamond 414, all prior operations are aborted and the program branches to the main display menu routine 206 (FIG. 3) through offpage connector 262. If the operator provides a "no" response, decision diamond 414 causes the program to branch back to interrupt main menu display 406.

If upon reviewing the video displayed interrupt menu 406 the operator chooses the "GOTO HOME" selection, the program branches to display box 418 where the operator is given a warning that the Emission Tomography Carousel or "ETC" will be moving to the home position. When the operator gives the proceed response, the program in a processing box 420 causes patient support 14 to move to the home position. Once patient support 14 is in the HOME position, the program returns to main menu routine 206 through offpage connector 262.

Finally, if the operator selects the "Continue Scan" option depicted on interrupt menu 406, the program branches to display box 424 where the operator is instructed by a message on monitor 108 to press "Enter" so that scanning can resume. The program then returns through terminal 426 to that part of the program in operation at the time the hotkey was pressed.

Figure 5:
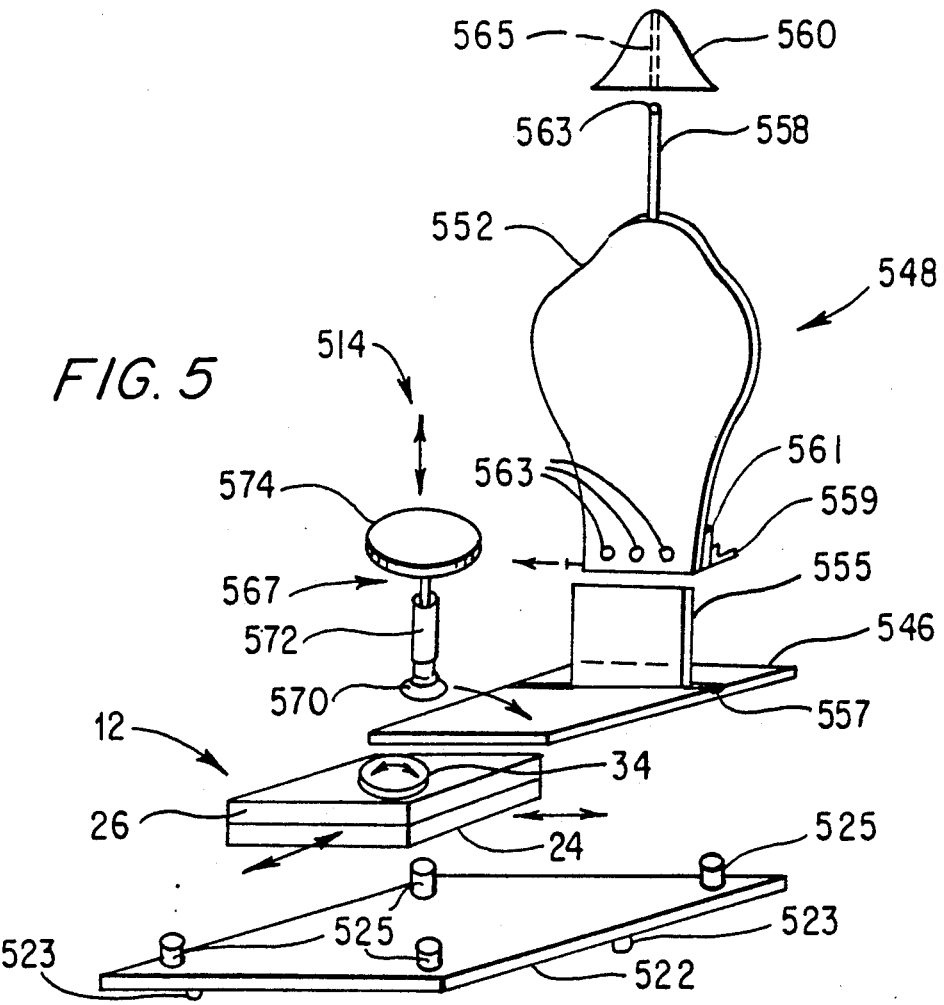
FIG. 5 is an exploded view of a reclinable tomography carousel for a sitting patient.

With reference now to FIGS. 5 and 6, a second embodiment of an emission tomography carousel 510 is depicted. Carousel 510 is comprised of positioning base 12 and a patient support 514. As with carousel 10 in FIG. 1, base 12 of carousel 510 includes an X-axis table 26 capable of moving patient support 514 in the x axis; Y-axis table 28 capable of moving patient support 514 in the y axis; and rotary table 34 for rotating patient support 514. Tables 26 and 28 can have exemplary dimensions of 21 inches square by about 7 inches thick. A patient support plate 546 is rigidly mounted to the rotating part of table 34 with means such as nuts and bolts (not shown). Support plate is preferably made of stainless steel and can have exemplary dimensions of 22 inches by 24 inches by ¼ inch.

Positioning base 12, is comprised of a movable platform 522. Platform 522 can be made of cold rolled steel and have exemplary dimensions of 24 inches by 36 inches by ¼ inch. Mounted on the bottom of platform 522 are two floor alignment pins 523 for mating with orifices (not shown), if desired, accurately located in the floor of the room in which the SPECT is being performed. Conventional hydraulic ball casters 525 on offset clamps are mounted on the upper side of platform 522 and can extend through orifices (not shown) in platform 522 to engage the floor. In this way, carousel 510 can be made both movable and accurately positionable with respect to a gamma camera.

Rigidly mounted perpendicular to support plate 546 is a unique patient support frame 548. Patient support frame 548 is comprised of a molded back support 552 that is described in greater detail hereinbelow. It is important that frame 548 be extremely strong and rigid, yet for mobility and ease of use that it also be light weight. In addition, frame 548 must be as non-interfering as possible to the radiation to be detected by gamma camera 18. It must also comfortably hold and restrain a patient in an immobile position for relatively long periods of time. Finally, it must have an overall shape that will permit a patient to be positioned to within an eighth of an inch of gamma camera 18 and then rotated and moved to numerous other orientations with respect to gamma camera 18.

Patient support frame 548 also is comprised of a riser plate 555 preferably made of stainless steel and having dimensions of 14 inches by 6 inches by ¼ inch. Riser plate 555 extends into a groove 557 in support plate 546 and is butt welded in place to provide greater structural rigidity. Bolted to the top of riser plate 555 (but shown unfastened in FIG. 5) is a hinge 559 to which in turn a mounting plate 561 is rigidly fastened with bolts 563. Mounting plate 561 has exemplary dimensions of 6 inches by 6 inches by ¼ inch. Patient back support 552 is bolted to mounting plate 561. Hinge 559 is a conventional breakaway hinge that extends the width of mounting plate 561 and riser plate 555.

Mounting plate 561 is held rigid to mounting plate with two spring loaded stop lock bolts 565 (only one being depicted in FIG. 6). A lanyard 566 is operatively connected to each lock bolt 565 so that the bolt can be readily disengaged from mounting plate 561. Two nitrogen compensating pistons 567 are mounted with universal connectors at each end to corresponding cloves 568 and 569 rigidly attached to patient support plate 546 and mounting plate 561, respectively. In the event of a patient emergency requiring support frame 548 to be rotated to a horizontal orientation, lanyard 565 need only be pulled. This in turn pulls bolts 565 against spring pressure out of engagement with the catch portion of the bolt and permits the weight of the patient to tilt or rotate back support 552 against the yielding opposition of pistons 567 through an angle of about 60 degrees.

Back support 552 is made of a core of "diviny" cell foam manufactured by the Airex Corporation. It is essentially a Styrofoam honeycomb, cellular structure that has a large number of very small holes completely therethrough. Back support 552 is made in a crafted mold of wood formed around a steel shell. The mold has an inner surface that is curvilinear to produce the desired shape of support 552.

Back support 552 is made by successively applying different layers to the mold to make a multilayer sandwich. First a gel coat is applied to the mold surface followed by a resin coat and then fiberglass. The foam core comes next and then the layers are repeated in reverse order: fiberglass, resin and a final outer layer of a gel coat. Molded into the bottom of back support is a wooden board (not shown) that gives the lower back portion of support 552 a flat rear surface that is out of view of gamma camera 18 and which is used to provide a means for securely attaching back support 552 to mounting plate 561. Exemplary thicknesses of support 552 are a base that is about 2½ inches thick and an upper body that is about ⅜ inch thick. The result is a fiberglass-/foam core support that is extremely lightweight, yet is extremely strong and rigid. The foam does not impeded the gamma radiation that is emitted by the patient during the SPECT procedure. Importantly, back support also provides a comfortable conforming support for the patient throughout the posterior rib cage.

Mated to and integral with back support 552 is a fiberglass arm-sling sting 558 having a terminal ring eye 563. Ring eye 563 permits the attachment of a conventional trapeze arm sling to which the patient's arm can be attached so that the arm can be elevated during certain cardiac procedures that require gamma camera 18 to clear the shoulder area. A head support 560 has a bore 565 therein to accommodate sting 558 and permit it to be mounted onto back support 552.

A patient stool 567 comprises a base 570 adapted to be rigidly bolted to support plate 542, a telescoping post 572 that permits height adjustment for different patients, and an upper cushioned seat 574. Stool 567 is mounted proximate to back support 552. Because stool 567 is out of the camera view, it can be made of any conventional material, such as steel.

The present invention has been described in terms of the foregoing presently preferred embodiments. It provides a system having extremely accurate positioning capabilities for use in an expensive procedure with conventional SPECT imaging equipment, but in the novel approach of having the patient move with respect to the camera. The present invention provides fully adequate degrees of freedom and motion to repeatedly, accurately circumscribe any locus of points with respect to the gamma camera. Because of their versatile, the present embodiments can be adapted to work with equipment already in place, and still produce results that are at least as accurate as conventional systems in which the detector moves. In addition, because of the ability to circumscribe an ellipse or an irregularly contoured shape, the present invention can provide better results because of the capability of keeping the area of interest within the center of the gamma camera field and at a minimal distance from the camera head, affording maximum organ and defect resolution. By firmly supporting the patient during the procedure, patient movement is minimized and motion artifacts are practically eliminated.

Obviously, other embodiments, variations, and modifications of the present invention would be apparent to those skilled in the art.

We claim:

1. An emission tomography carousel system for use with a stationary radiation detector comprising:
   a platform for receiving a patient who has a body that defines a vertical axis through the center thereof;
   movable mounting means for supporting said platform;
   means for moving said mounting means in translational movements in orthogonal directions;
   means for rotating said mounting means; and
   automatic programmable means for directing the movement of said mounting means about a predetermined locus of points such that said platform moves in a predetermined manner with respect to the stationary radiation detector so as to keep a point of interest that is off the vertical axis of the patient in substantially the center of the locus of points.

2. An emission tomography carousel system as claimed in claim 1 wherein said platform comprises a seat, and
   a back support made of a lightweight material that is rigid and substantially transparent to gamma radiation.

3. A method of emission tomography for investigating an area of interest in a patient utilizing a stationary radiation detector and a patient that moves relative to the detector, the method comprising:
   securely mounting a patient onto a movable platform;
   moving said platform in both translational and rotational directions with respect to the stationary detector such that all aspects of the patient are presented to the detector while keeping the area of interest of the patient in substantially the center of the locus of points through which said platform has moved.

4. An emission tomography carousel for use with a detector of a known type of radiation, said carousel comprising
   a foundation supported by a floor;
   a patient support;
   moving means mounted to said foundation for moving said patient support for both translational motion and rotational motion such that a point of interest that is off the vertical axis of the patient can be kept in substantially the center of the locus of points through which said patient support is moved;
   wherein said patient support comprises a base plate connected to said moving means, and a vertical frame mounted to said base plate, said frame being made from a material that is transparent to the known radiation, and said frame being rigid and curvilinear in shape.

5. An emission tomography carousel as claimed in claim 4 and further including means for securing a patient to said frame so as to restrain the movement of the patient.

6. An emission tomography carousel as claimed in claim 4 and further including means for pivotally attaching said frame to said base plate, said pivotally attaching means comprising a hinge, releasable locking means for retaining said frame in a vertical position when engaged and for permitting said frame to rotate when disengaged, and motion control means connected between said frame and base plate for slowing the pivoting of said frame when said locking means is disengaged.

* * * * *